United States Patent
Wolff et al.

(10) Patent No.: US 10,130,753 B2
(45) Date of Patent: Nov. 20, 2018

(54) LOCKING SYSTEM FOR LOCKING A MEDICAL DEVICE

(71) Applicant: Fresenius Vial SAS, Brézins (FR)

(72) Inventors: Rémy Wolff, Morette (FR); Frederic Couillaud, Brézins (FR)

(73) Assignee: Fresenius Vial SAS, Brezins (FR)

( * ) Notice: Subject to any disclaimer, the term of this patent is extended or adjusted under 35 U.S.C. 154(b) by 668 days.

(21) Appl. No.: 14/441,661

(22) PCT Filed: Oct. 28, 2013

(86) PCT No.: PCT/EP2013/072480
§ 371 (c)(1),
(2) Date: May 8, 2015

(87) PCT Pub. No.: WO2014/072196
PCT Pub. Date: May 15, 2014

(65) Prior Publication Data
US 2015/0273138 A1 Oct. 1, 2015

Related U.S. Application Data

(60) Provisional application No. 61/724,488, filed on Nov. 9, 2012.

(30) Foreign Application Priority Data

Nov. 9, 2012 (EP) ...................................... 12306389

(51) Int. Cl.
*A61M 5/14* (2006.01)

(52) U.S. Cl.
CPC ............ *A61M 5/14* (2013.01); *A61M 5/1413* (2013.01); *A61M 5/1415* (2013.01);
(Continued)

(58) Field of Classification Search
CPC .... A61M 5/14; A61M 5/1413; A61M 5/1415; A61M 2205/18; A61M 2205/50;
(Continued)

(56) References Cited

U.S. PATENT DOCUMENTS 2,407,269 A * 9/1946 Hannant ............... F17C 13/002
74/502
3,436,860 A * 4/1969 James ................... E05D 15/507
16/232
(Continued)

FOREIGN PATENT DOCUMENTS

EP 0477551 4/1992

*Primary Examiner* — Amber R Anderson
*Assistant Examiner* — Nahid Amiri
(74) *Attorney, Agent, or Firm* — Occhiuti & Rohlicek LLP

(57) ABSTRACT

A locking system for locking a medical device at a holding structure, the medical device and the holding structure each provided with retaining structures which can cooperate with one another. The locking system includes a retaining lock for retaining the medical device when connected to the holding structure and being movable by a first manual control mechanism between a retaining position, in which the lock retains the medical device on the holding structure, and a free position, in which the lock does not retain the medical device on the holding structure. The locking system also includes a security lock which is movable by an automatic control device between active and inactive positions. The security lock, in the active position, prevents the medical device from being removed from the holding structure. In the inactive position, the security lock does not prevent the medical device from being removed from the holding structure.

27 Claims, 8 Drawing Sheets

(52) U.S. Cl.
CPC ..... *A61M 2205/18* (2013.01); *A61M 2205/50* (2013.01); *A61M 2209/082* (2013.01); *A61M 2209/084* (2013.01); *Y10T 403/581* (2015.01)

(58) Field of Classification Search
CPC ....... A61M 2209/082; A61M 2209/084; Y10T 403/581; Y10T 403/591; Y10T 403/593; Y10T 403/598; Y10T 403/599; Y10T 403/602; Y10T 403/604; Y10T 403/7039; F16B 2/12; F16B 21/07; F16B 21/0763; F16B 21/18; F16B 21/186
USPC .............................. 403/315–318, 322.3, 361
See application file for complete search history.

(56) References Cited

U.S. PATENT DOCUMENTS

| | | | | |
|---|---|---|---|---|
| 4,088,436 A * | 5/1978 | Alferes | ............... | F16L 37/23 137/517 |
| 4,126,340 A * | 11/1978 | Pelcin | ............... | G05G 15/00 292/1 |
| 4,256,010 A * | 3/1981 | Petrie | ............... | F16B 21/18 411/518 |
| 4,280,523 A * | 7/1981 | Norton | ............... | F16L 37/00 137/74 |
| 4,500,118 A * | 2/1985 | Blenkush | ............... | F16L 33/223 285/104 |
| 4,541,457 A * | 9/1985 | Blenkush | ............... | F16L 37/0841 137/614.05 |
| 5,033,777 A * | 7/1991 | Blenkush | ............... | F16L 37/0841 285/317 |
| 5,409,322 A * | 4/1995 | Horikawa | ............... | B23B 31/265 279/89 |
| 5,625,537 A | 4/1997 | Neuder | | |
| 5,628,148 A * | 5/1997 | Beutler | ............... | E05B 15/0006 292/19 |
| 5,642,960 A * | 7/1997 | Salice | ............... | E05D 5/02 403/328 |
| 5,845,943 A * | 12/1998 | Ramacier, Jr. | ............... | F16L 37/0841 137/614.04 |
| 5,855,040 A * | 1/1999 | Lin | ............... | E05D 5/10 16/50 |
| 5,971,019 A * | 10/1999 | Imai | ............... | F16L 37/23 137/614.04 |
| 6,112,855 A * | 9/2000 | Camacho | ............... | F16L 37/0841 184/1.5 |
| 6,997,181 B2 * | 2/2006 | Fletcher | ............... | A62B 18/086 128/201.28 |
| 7,153,296 B2 * | 12/2006 | Mitchell | ............... | A61M 39/10 604/533 |
| 7,726,378 B1 * | 6/2010 | Savon | ............... | E06B 3/485 16/258 |
| 9,157,560 B2 * | 10/2015 | Rehder | ............... | F16L 37/0841 |
| 9,597,475 B2 * | 3/2017 | McPhearson | ............... | A61M 16/0816 |
| 2005/0074280 A1 * | 4/2005 | Chen | ............... | F16B 21/071 403/329 |
| 2014/0187866 A1 * | 7/2014 | Kaye | ............... | A61B 1/00137 600/154 |
| 2016/0067655 A1 * | 3/2016 | Roberts | ............... | C12G 1/00 261/66 |
| 2016/0361801 A1 * | 12/2016 | Wang | ............... | B25B 23/0028 |
| 2017/0291266 A1 * | 10/2017 | Haruna | ............... | B23K 37/053 |

\* cited by examiner

LOCKING SYSTEM FOR LOCKING A MEDICAL DEVICE

CROSS REFERENCE TO RELATED APPLICATIONS

This application is a National Stage of International Application No. PCT/EP2013/072480 filed on Oct. 28, 2013, which claims priority to European Application No. 12306389.3 filed on Nov. 9, 2012 and U.S. Provisional Application No. 61/724,488 filed on Nov. 9, 2012, the contents of which are hereby incorporated by reference in their entirety.

BACKGROUND

The invention relates to a locking system for locking a medical device on a holding structure wherein the medical device and the holding structure are each provided with retaining elements which can cooperate with one another. The invention relates also to a medical device and a holding structure comprising the locking system of the invention and a locking method applied to the locking system of the invention.

In medical treatment, it is not an uncommon situation that a plurality of medical devices is connected to a same patient. These medical devices can for example be perfusion pumps or syringe pumps. They may be attached to a holding structure, like a rack, in proximity of the patient's bed.

A pump may operate alone or a plurality of medical devices may interoperate. Two pumps may for example operate alternatively or a pump delivers a product with a certain debit while another pump delivers a second product with another debit depending on the debit of the first pump. Preferably none of the medical devices should be removed without special reason while it is operating alone or in combination with at least one other medical device. This requires the medical staff to be very attentive and, in case of multiple pumps, to control a whole system before removing a medical device from the system.

SUMMARY

The objective of the invention is to provide a system which reduces the risk of detaching a medical device from a holding structure by mistake.

According to the invention this objective is achieved in that the locking system comprises a first retaining lock for retaining the medical device when connected to the holding structure, wherein the first retaining lock is movable by a first manual control mechanism between a retaining position, in which the first retaining lock retains the medical device on the holding structure to which it is connected, and a free position, in which the first retaining lock does not retain the medical device on the holding structure to which it is connected;

a security lock which is movable by an automatic control device between an inactive position and an active position, wherein the security lock, in the active position, prevents the medical device from being removed from the holding structure to which it is connected, and in the inactive position, the security lock does not prevent the medical device from being removed from the holding structure to which it is connected.

This security lock is controlled for example by the electronic control unit used for controlling the operation of the medical device either alone or in combination with other medical devices. If the medical device must not be removed, the security lock is placed in the active position. As soon as the task of the medical device is achieved and it can be removed from the rack, the electronic control unit makes the security lock pass in the inactive position. There is no more human error possible.

In order to allow the medical device to be voluntarily removed, despite knowing of the medical staff that the medical device is still in operation, it is preferable to provide the locking system with a second manual control mechanism for circumventing the effect of the security lock so that the medical device may be removed from the holding structure to which it is connected even if the security lock is in the active position. In order to remove the medical device from the holding structure, it is required that the medical staff actions voluntarily a second manual control mechanism to enable him to get round the effect of the security lock. It is therefore not possible that unlocking occurs inadvertently, but only by a voluntary action realized in full knowledge. This may be necessary if the medical device does not operate correctly or if its electric power supply has been cut before the electronic command has sent a signal to the automatic control device.

In order to prevent the medical staff of an attempt to remove a medical device against the effect of the security lock, a detector may be provided for detecting the active position of the security lock. In this case, a signal emitting device may be provided for emitting a visual or audible signal when the detector detects that the security lock has been circumvented.

The automatic control device for moving the security lock may comprise an actuator, preferably a linear actuator.

In a first embodiment, the locking system comprises a second retaining lock for retaining the medical device when connected to the holding structure, wherein the second retaining lock is movable by the security lock between a retaining position, in which the second retaining lock retains the medical device on the holding structure to which it is connected, and a free position, in which the second retaining lock does not retain the medical device on said holding structure.

Thus, the first retaining lock secures the medical device connected to the rack. It is sufficient to unlock this first retaining lock in order to remove the medical device. However, this is only possible if the second retaining lock is also in the free position. In the contrary case, the second retaining lock retains the medical device. In the latter case, the medical staff knows that the medical device operates and should not to be removed unless for an important reason. However, if the replacement of the medical device is required and if the locking system is provided with a second manual control mechanism, the medical staff is not only required to operate the first manual control mechanism of the first retaining lock, but also the second manual control mechanism of the second retaining lock in order to get round the effect of the security lock.

Where the first embodiment is provided with a second manual control mechanism for circumventing the effect of the security lock, this second mechanism may comprise either a non-electric device being able to be actuated from the outside of the medical device and of the holding structure, preferably a pull-knop, wherein the non-electric device is coupled to the second retaining lock, and a spring located between the second retaining lock and the security lock, or an electrical device being able to be actuated from the outside of the medical device and of the holding structure.

The first manual control mechanism for moving the first retaining lock may comprise either a non-electric device, which is accessible from the outside of the medical device and of the holding structure, preferably a pull-knop, wherein the non-electric device is coupled to the first retaining lock, or an electric device which can be actuated from the outside of the medical device and of the holding structure.

The first retaining lock can be held, preferably by a spring, in the locking position in absence of any external influence.

The first retaining lock and/or the second retaining lock may comprise each a latch, which is located at the retaining element of the medical device or of the holding structure, wherein the latches are shaped and located in such a way to be able to engage each a corresponding recess provided at the retaining element of the holding structure or of the medical device, when the medical device is connected to such a holding structure. Other kind of locking elements known to a person skilled in the art are of course also possible.

In a second embodiment of the invention, the security lock, in the active position, prevents the first manual control mechanism from moving the retaining lock in the free position.

In a first alternative, the first manual control mechanism comprises a push button a transmission linkage and a control element, wherein the push button can move between un standby position and a pushed-in position, wherein the transmission linkage can move between a retracted position and an advanced position, wherein a spring tends to return the transmission linkage into the retracted position, wherein the transmission linkage, in the retracted position, pushes the push button into the standby position, wherein the push button, in the pushed-in position, pushes the transmission linkage into the advanced position against the effect of the spring operating on said transmission linkage, wherein the control element can move from a locking position, in which it locks the retaining lock in the retaining position, and a unlocking position, in which it does not lock the retaining lock in the retaining position, wherein a spring tends to return the control element in the locking position, and wherein the transmission linkage, when moving from the retracted position to the advanced position, moves the control element in the unlocking position.

In a second alternative, the first manual control mechanism comprises a push button and a transmission linkage, wherein the push button can move between un standby position and a pushed-in position, wherein the transmission linkage can move between a retracted position and an advanced position, wherein a spring tends to return the transmission linkage into the retracted position, wherein the transmission linkage, in the retracted position, pushes the push button into the standby position, wherein the push button, in the pushed-in position, pushes the transmission linkage into the advanced position against the effect of the spring operating on said transmission linkage, and wherein the transmission linkage, when moving from the retracted position to the advanced position, moves the retaining lock in the free position.

For both alternatives, the security lock, in the active position, is situated in the passage used by the push button to pass from the standby position to the pushed-in position such that the push button comes into abutment against the security lock before reaching the pushed-in position.

In order to circumvent the effect of the security lock, the push button may be designed to be able to move beyond the standby position into a raised position opposite to the pushed-in position, wherein in the raised position of the push button, the transmission linkage may be actuated from the outside of the medical device and of the holding structure although the security lock is in the active position.

For both embodiment, the first retaining lock, the second retaining lock if available, and the security lock may be located either at the fixation element of the medical device or at the fixation element the holding structure.

The invention also relates to a medical device and to a holding structure comprising the locking system of the invention.

The invention also relates to a method for controlled locking of a medical device with a holding structure by means of a locking system according to the invention. For that purpose, the security lock is moved by the automatic control device from the inactive position to the active position at the beginning of a procedure during which the medical device should not be removed from the holding structure, and the security lock is moved by the automatic control device from the active position to the inactive position when the medical device can be removed from the holding structure;

the automatic control device being controlled by the electronic control unit.

Preferably, the effect of the security lock may be circumvented by actuating the second manual control mechanism. This may be achieved by moving the second retaining lock in the free position (first embodiment) or by moving the push button from the standby position to the raised position so as to release access to the linkage from the outside of the medical device and of the holding structure (second embodiment).

The invention is described more in detail hereafter with reference to the figures which illustrate schematically a rack as holding structure and a pump provided with the locking system of the invention as medical device.

DETAILED DESCRIPTION

Figure 1:
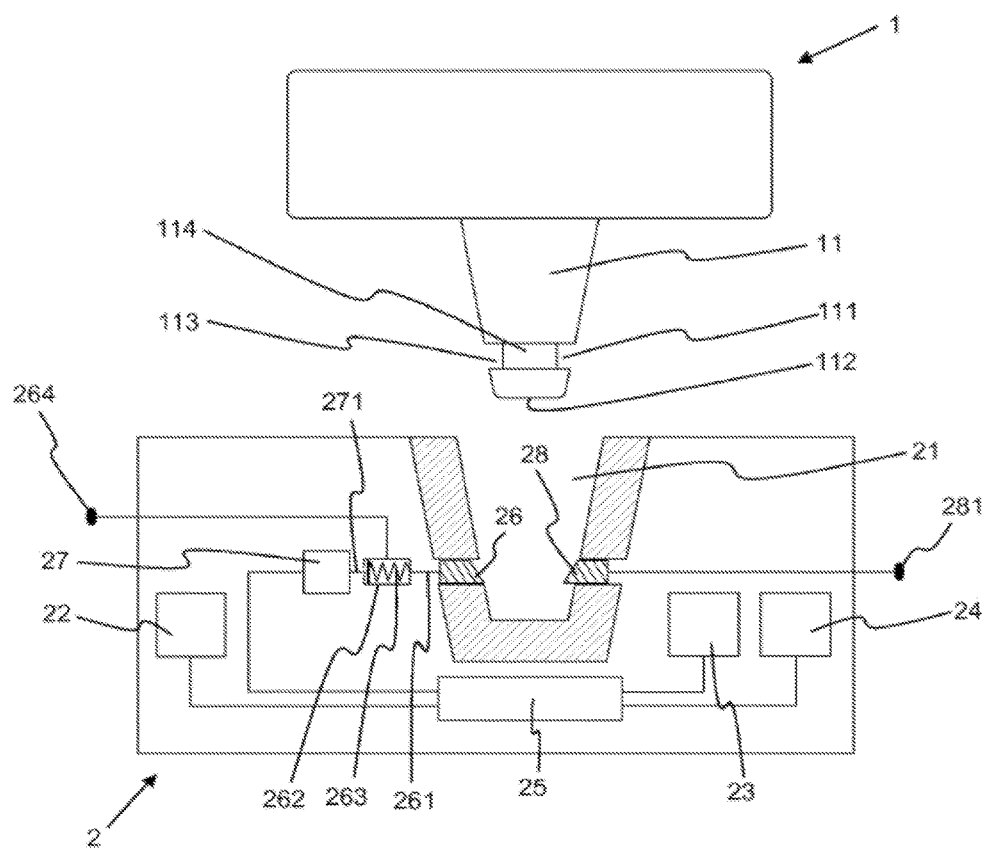
FIG. 1: a schematic view of the rack and of the medical device of a first embodiment before the insertion of the medical device into the rack.
Figure 2:
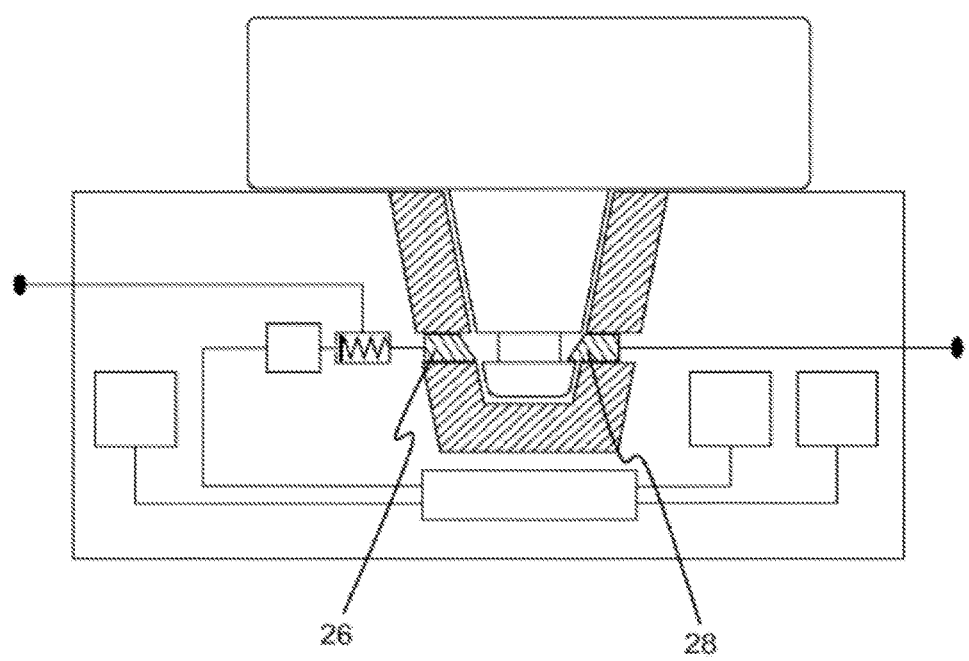
FIG. 2: the same view as in FIG. 1, the medical device being connected to the rack and the second retaining lock being inactivated.
Figure 3:
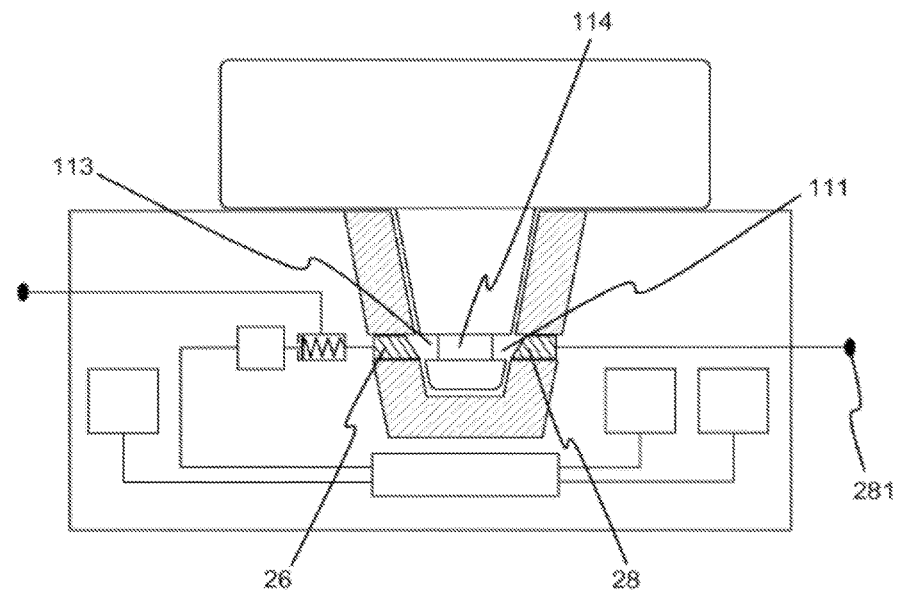
FIG. 3: the same view as in FIG. 2, the first retaining lock being also inactivated.
Figure 4:
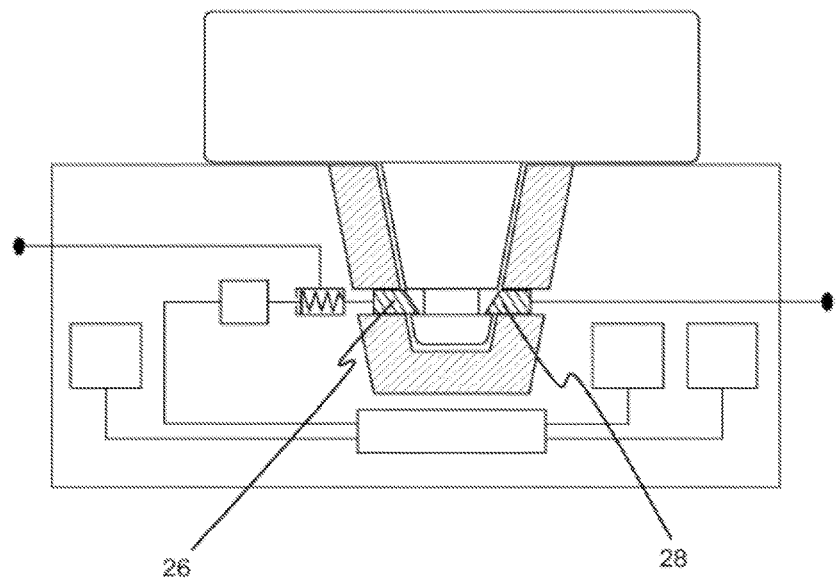
FIG. 4: the same view as in FIG. 2, the second retaining lock and the first retaining lock being activated.
Figure 5:
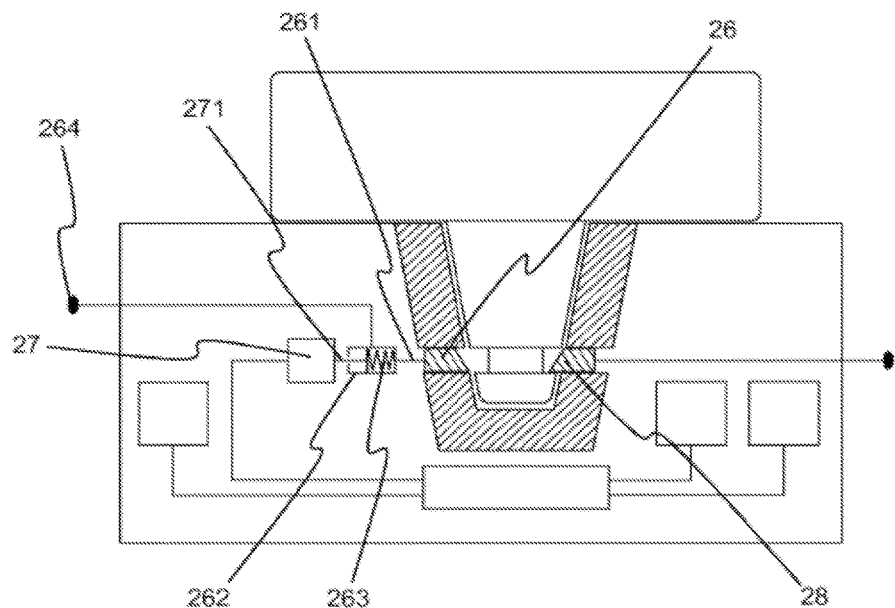
FIG. 5: the same view as in FIG. 4, the second retaining lock being manually circumvented against the effect of the automatic control device.
Figure 6:
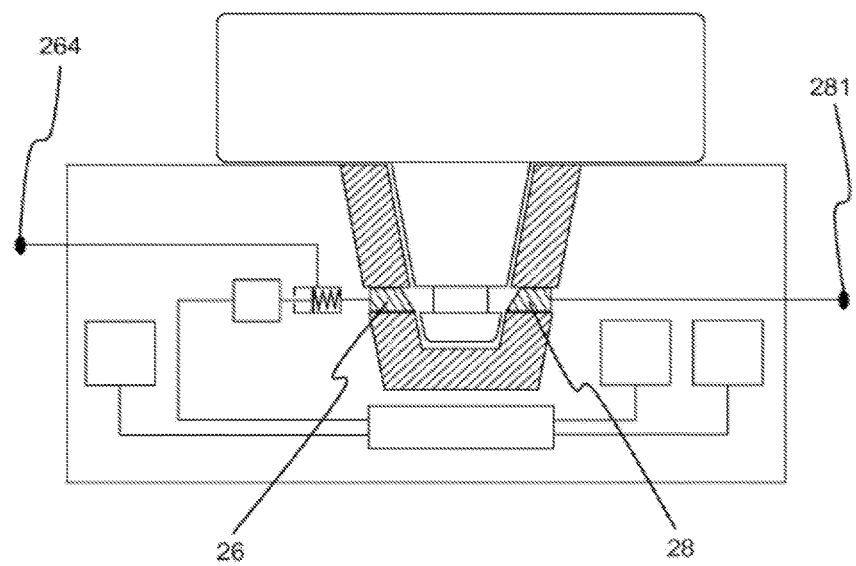
FIG. 6: the same view as in FIG. 5, the first retaining lock being also inactivated.
Figure 7:
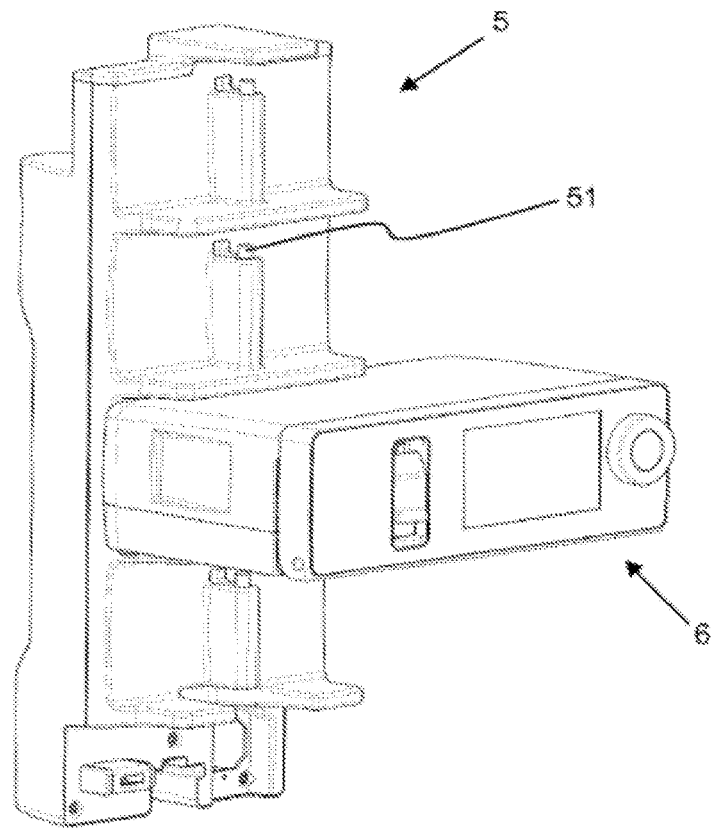
FIG. 7: a perspective view of a rack of the second embodiment on which is fixed a medical device of a second embodiment.
Figure 8:
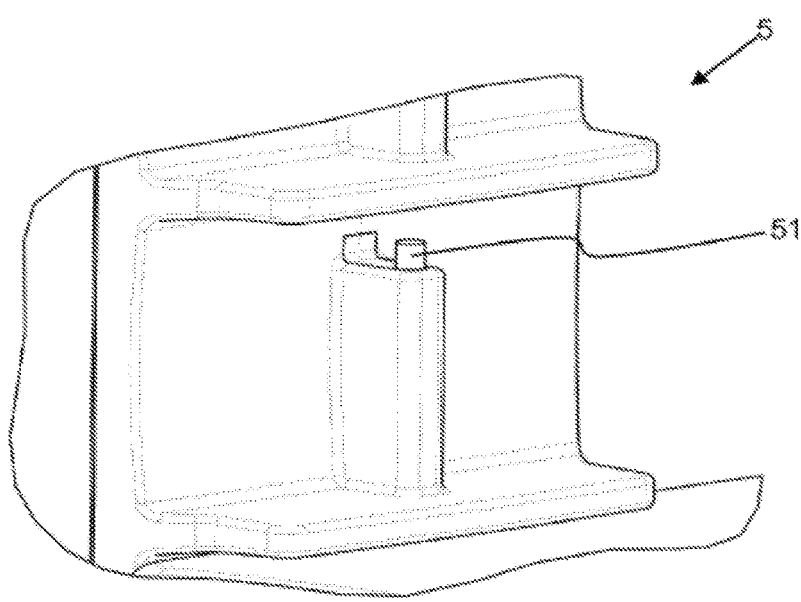
FIG. 8: an enlarged view of the rack of FIG. 7 showing the fixing plug.
Figure 9:
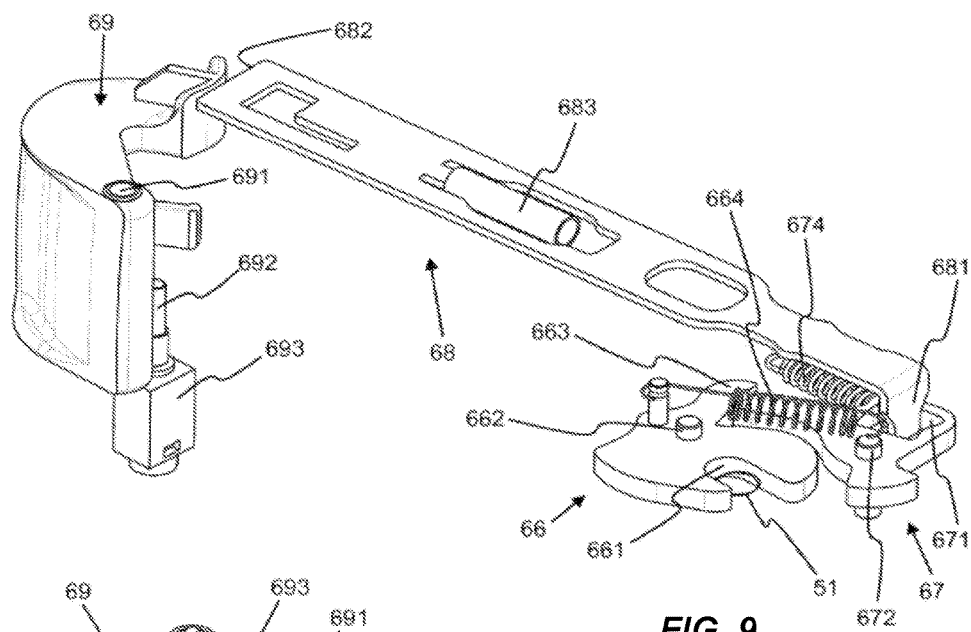
FIG. 9: a perspective top view of the different elements of the locking system.
Figure 10:
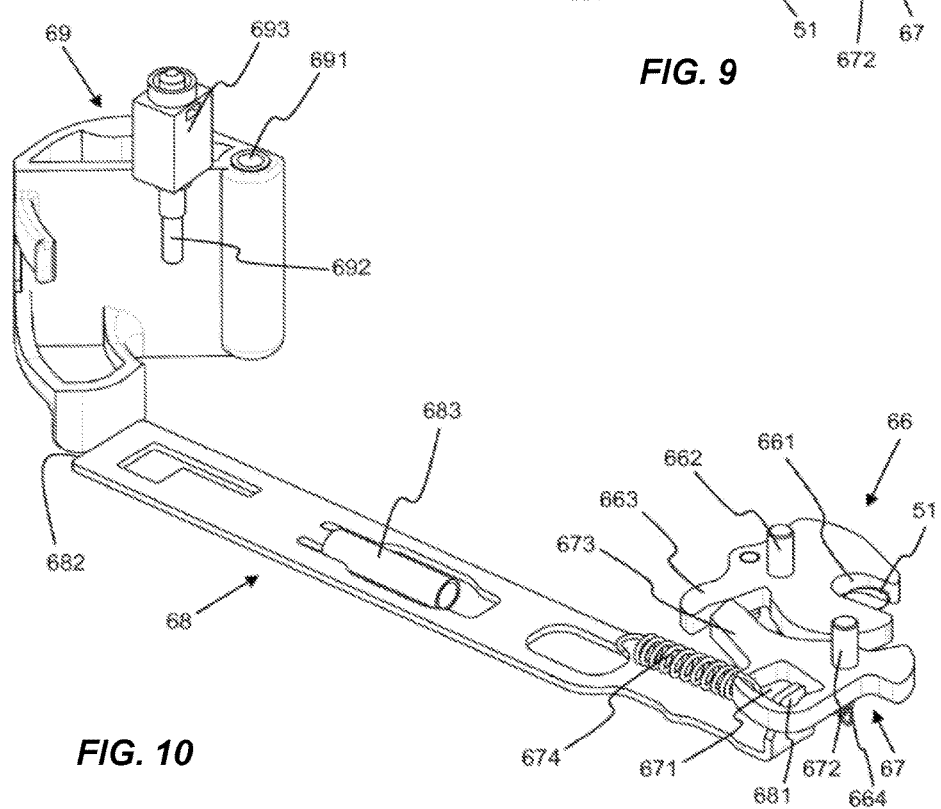
FIG. 10: a perspective bottom view of the locking system of FIG. 9.

The invention is described hereafter more in detail with reference to two embodiments.

The figures illustrate schematically the operation mode of the device according to the invention. The shown shape and size of the retaining elements are not limiting characters. Therefore any shape and size, which allows retaining of the medical device on the holding structure, is possible to be used and the given shape and size are only used as an example. A person skilled in the art would be able to adapt the locking system of the invention to any other retaining elements used in this technical field.

The figures show a fixing plug 11, 51 of a rack 1, 5 for holding medical devices such as infusion pumps. This plug 11, 51 constitutes the retaining element of the holding structure. A medical device 2, 6, which can be connected to the rack, in the present case a pump, is also shown. In order to connect the pump with the rack, the pump comprises a retaining element, which is located at the back side of the medical device. This retaining element cooperates with the fixing plug 11, 51 and is shaped in form of a socket 21.

The pump is also provided with a pumping mechanism 22, 62, a display 23, 63 and a control panel 24, 64. An electronic control unit 25, 65, for example a microprocessor, allows to control the operation of the pump and to exchange data with other pumps or with an external central unit which controls the coordinated operation of a plurality of medical devices.

Generally, it is not allowed to remove the medical device before it has terminated its operation, regardless whether it is operating alone or in combination with other medical devices. If the pump operates with other medical devices, it is not to be removed at any time. Even if it appears to be inactive, it is possible that it awaits a signal from the central control unit in order to be activated. It must be ensured that the medical staff does not remove the medical device by mistake.

The FIGS. 1 to 6 refer to the first embodiment, the FIGS. 7 to 12 to the second embodiment. In the first embodiment, the fixing plug 11 is substantially parallel to the approach movement of the medical device toward its location in the holding structure. In the second embodiment, the fixing plug 51 is no longer parallel to this approach movement, but substantially perpendicular thereto.

The first embodiment is now explained in more detail with the help of FIGS. 1 to 6.

In order to allow the medical staff to secure the medical device on the rack, the fixing plug of the rack is provided with a first recess 111, into which a first latch 28 can penetrate, wherein the first latch is located at the socket 21. This first latch 28 is movable between a retaining position, shown for example in FIG. 1, in which it penetrates into the cavity of the socket 21 and a free position, shown for example in FIG. 3, in which the latch does not penetrate into said cavity. A control device which is not represented, e.g. a spring, ensures that in absence of any external influence the first latch is in the retaining position, as shown in FIG. 1. The side of the latch which penetrates into the cavity forms an inclined plan directed to the insertion opening of the socket.

The first latch is fixed to a first manual control mechanism, for example in form of a first pull-knop 281, to allow the medical staff to move the first latch in the free position against the effect of the spring (not shown).

To prevent the medical staff from removing the medical device while it is in operation, a second latch 26 is provided which is located at the retaining element of the medical device, in this embodiment at the socket 21. This second latch can move between an free position, which in this embodiment corresponds to a retracted position, represented for example in FIG. 1, and a retaining position, shown in FIG. 4, in which it penetrates into the cavity of the socket 21. The penetrating part of the latch, like the first latch, is chamfered in order to form an inclined plane directed to the insertion opening of the socket.

The second latch 26 is fixed on the end of a rod 261. The other end of the rod is fixed to a box 262 in which a spring 263 is enclosed between the wall on which the rod 261 is fixed, called front wall, and the opposite wall, called back wall. An actuator 27, which is controlled by the electronic control unit 25, moves this second latch from one position to the other. This actuator may be e.g. a linear actuator. It moves a piston 271 which penetrates into the box 262 through an opening in the back wall. The front end of the piston is provided with a disk which pushes against the side of the spring directed to the back end of the box. Thus, the spring 263 is supported by its first end against the front wall of the box 262 and by its second end against the disk of the piston 271. The spring 263 is designed in such a way that in absence of external influence, when the piston 271 moves in direction of the socket 21, the spring 263 transmits this movement to the box 262 and to the rod 261 without being deformed. The rod 261 then moves the second latch to the retaining position.

Upon mounting the pump on the rack, the fixing plug 11 enters the cavity of the socket 21 and the rounded front side 112 of the fixing plug hits the inclined plane of the first retaining lock 28, wherein this first retaining lock is pushed into the wall of the socket 21 towards its free position. As soon as the first recess 111 of the plug is aligned with the first latch 28, the latter engages the recess 111 due to the effect of the non-shown spring and thus returns to its initial position or at least to a position in which the plug 11 is effectively locked (retaining position).

Thus, the medical device 2 is well secured on the rack. This is the position shown in FIG. 2.

When the control unit 25 starts the operation or has received the information that the medical device is operating, either alone or in combination with other devices, it sends a signal to the actuator 27 in order to make it move the piston 271 in the active position, and thus move the spring 263, the box 262, the rod 261 and the second latch 26 in the retaining position. This is the situation shown in FIG. 4.

As soon as the control unit ends the operation or has received the information that the medical device has terminated its operation, it sends a signal to the actuator in order to make it move the piston 271 to the inactive position, thus moving the second latch 26 in the free position. This is the situation shown in FIG. 2.

In order to remove the pump from the rack, the operator has to inactivate the first latch 28, e.g. by pulling on the first pull-knob 281, which is accessible from the outside of the pump. This is the situation shown in FIG. 3. If the second latch 26 is in the free position, it is then possible to remove the medical device from the rack.

It may be necessary to remove a medical device even if it is still operating or in case the automatic control device has set the second retaining lock 26, through the piston 271, in its retaining position for other reasons. This may e.g. be required if there is a dysfunction of the medical device. In this case, the second latch 26 is however in the retaining position and prevents removing the medical device by unlocking the first latch 28 only. It is then necessary to enable the medical staff to get round the effect of the piston 271 so that the staff may act directly as well on the first latch 28 as on the second latch 26. It is e.g. possible to provide an unlocking button which sends a signal to the electronic control unit in order to move the piston in the inactive position and thus to unlock the second latch in contrast to the information stored in the control unit. In the example described here, a second hand-operated unlocking device in form of a second pull-knob 264 accessible to the medical staff is e.g. fixed to the box 262. If this second pull-knob is pulled when the second latch is in the retaining position (see FIG. 4), the box 262 is moved away from the socket 21 by compressing the spring 263 against the disk of the piston 271 of the actuator. This is the situation shown in FIG. 5. It is possible to remove the medical device from the rack although it was operating, either alone or in combination with other medical devices.

As soon as the two pull-knobs 264, 281 are released, the two latches return to their respective retaining position.

The second recess 113 is located in such a way that the second latch 26 is facing the second recess 113 when the medical device is connected to the rack and the first latch 28 engages the first recess 111. In the example shown here, the two latches are facing each other and the two recesses 111, 113 are equidistant from the front face 112 of the plug. In fact, an annular recess 114, which fulfills the function of the two recesses and into which the two latches can enter, has been provided instead of two distinct recesses.

Due to the inclined planes of the two latches and the spring loading of both of the latches, it is possible to connect a new medical device even if the second latch is in the retaining position, that is to say even if the automatic control device 27 is set to maintain the piston in the active position. The fixing plug 11 upon its insertion into the socket 21 pushes aside the two latches 26, 28, with its front face 112 against the force of the spring 263 enclosed in the box 262 and against the force of the spring not shown which acts on the first latch.

The second embodiment is now explained in more detail with the help of FIGS. 7 to 12. FIGS. 7 to 11 show a first alternative, FIG. 12 a second alternative. In both alternatives, the fixing plug 51 is no longer parallel to the approach movement of the medical device but substantially perpendicular thereto. A retaining lock 66 in form of a hook is provided, which is located at the retaining element 61 of the medical device. This retaining lock 66 can be moved between an free position, which in this embodiment corresponds to a pivoted position, shown for example in FIGS. 11a and 12b, and a retaining position, shown for example in FIGS. 11b and 12a.

In the first alternative shown in the FIGS. 7 to 11, the retaining lock 66 is provided with a longitudinal slot 661 emerging on the edge of the retaining lock and in which the fixing plug 51 enters when the medical device is fixed to the rack and the retaining lock 66 is in the retaining position. The retaining lock 66 can pivot about an axis 662 fixed with respect to the housing of the medical device. In the pivoted position, i.e. the free position, of the retaining lock, the longitudinal slot 661 is inclined, for example by 45°, with respect to the direction of introduction of the medical device in the rack with the access opening of the slot placed in the path followed by the fixing plug during the introduction or the removing of the medical device in the rack, while in the retaining position the slot is perpendicular to the introduction movement, or is even inclined beyond the perpendicular so that its access opening is no longer in the path followed by the fixing plug during introduction or the removing of the medical device. The retaining lock is also provided with a guide finger 663, referred to as the first guide finger, the end of which acts as a first follower by bearing on a first guide surface that will be presented below. The lateral surface of the first guide finger 663 acts as a second guide surface for a second follower that will also be presented below. A first spring 664 tends to return the retaining lock 66 into the pivoted or free position.

In this first alternative, the movement of the retaining lock 66 between the free position and the retaining position is controlled by a control element 67. This control element can pivot between a locking position shown in FIG. 11b and an unlocking position shown in FIG. 11a. It is provided with a recess 671 in which the end of a transmission linkage 68 presented below can enter. This substantially rectangular-shaped recess has in particular a thrust edge against which the end of the transmission linkage can bear. The control element can pivot about an axis 672 fixed with respect to the housing of the medical device. It is provided with a guide finger 673, referred to as the second guide finger, the end of which serves as a second follower and the lateral surface of which constitutes the first guide surface mentioned previously. A second spring 674 tends to return the control element 67 into the locking position.

In the second alternative shown in FIG. 12, the retaining lock 66 is provided with a retaining finger which is placed behind the fixing plug 51 when the hook is in the retaining position, or is situated out of the approach path of the fixing plug into the retaining element 61 of the medical device when the hook 66 is in the free position. A spring which is not shown tends to return the hook of this second alternative in the retaining position. The end of the transmission linkage bears directly on the retaining lock 66 against the effect of the non-shown spring. The front edge of the retaining finger is inclined in such a way that the fixing plug 51, during the penetration movement of the medical device in the location, slides over the inclined surface front edge and thus forces the retaining lock 66 to pivot about the axis 662 counter to the effect of the first spring (not shown).

In both alternatives, a transmission linkage 68 is housed in the housing of the medical device so as to be able to move in translation between a retracted position and an advanced position. The first is shown schematically for example in FIG. 12a, the second in FIG. 12b. The transmission linkage 68 is provided at one of its ends with a first bearing surface 681 sized so as to be able to enter the recess 671 of the control element 67 while being able to move inside and where applicable bear against the thrust edge. The other end of the linkage is provided with a second bearing surface 672 against which a push button 69 presented below can bear. A third spring 683 shown as a cylinder in FIGS. 9 and 10 and schematically in FIG. 12 tends to push the transmission linkage into the retracted position.

A push button 69 is housed on the housing of the medical device so as to be accessible to the medical worker. This push button can pivot about an axis 691 between a pushed-in position shown schematically in FIG. 12b and as standby position shown schematically for example in FIG. 12. It will be seen below that it can pivot beyond the standby position into a raised position opposite to the pushed-in position. The second bearing surface 682 of the transmission linkage is in contact with the push button when the latter is situated in the standby position or in the pushed-in position. When the transmission linkage is in the retracted position, it pushes the push button, under the effect of the third spring, into the standby position.

A security lock 692, in form of a rod, is provided in the housing for preventing the push button 69 from reaching the pushed-in position from the standby position. This security lock can move between an inactive position, in which it does not interfere with the movement of the push button, and an active position in which it is situated in the passage used by the push button to pass from the standby position to the pushed-in position. The push button, in abutment against the security lock, cannot therefore leave the standby position in the direction of the pushed-in position, or at least is prevented from going to the pushed-in position. An actuator 693 connected to the electronic control unit controls the movement of the security lock.

The second embodiment functions as follows.

Let it be assumed that a medical device must be fixed to a rack, the locking system of the first alternative being in an initial position in which
  the security lock 692 is in the inactive position,
  the push button 69 is in the standby position,
  the transmission linkage 68 is in the retracted position, its first bearing surface 681 somewhere inside the recess 671,
  the control element 67 is in the unlocking position, and
  the retaining lock 66 is in the free position.

Figure 11A:
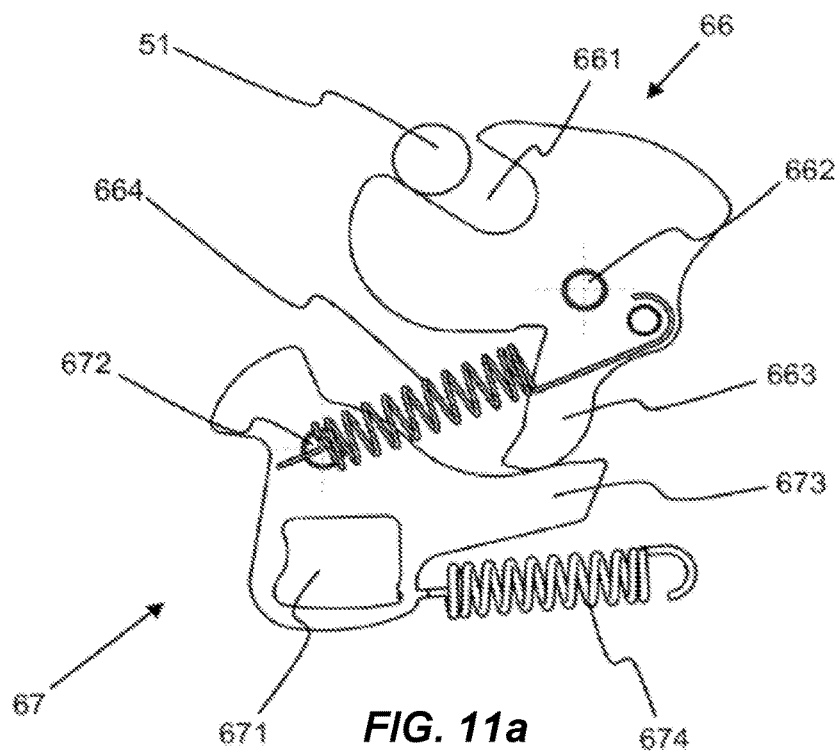
FIG. 11: a top view of the retaining lock and of the control element (a) in free position and (b) in retaining position.
Figure 11B:
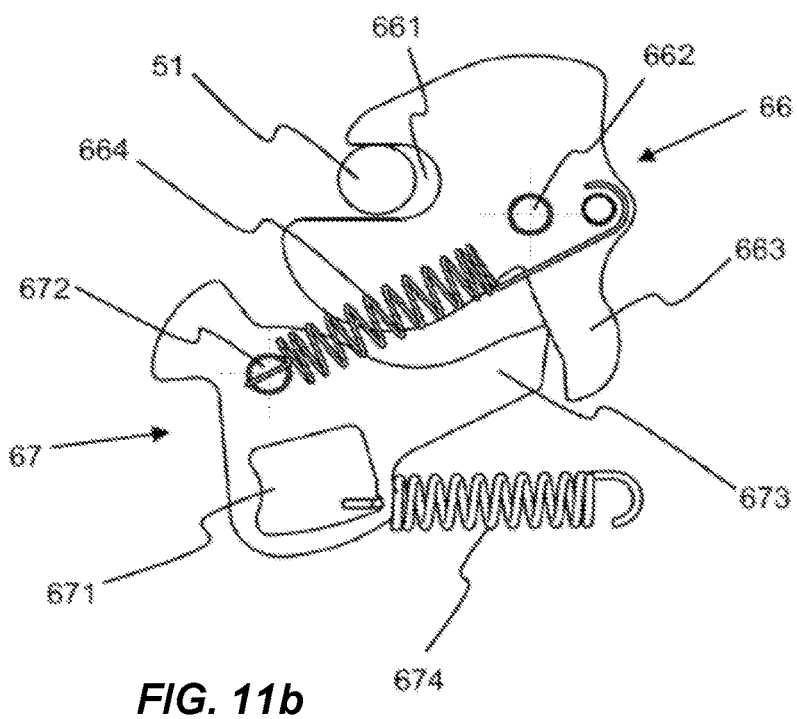

This is the situation shown in FIG. 11a. In this position, the end of the first guide finger 663, fulfilling the role of a follower, is in abutment against the first guide surface formed by the lateral edge of the second guide finger 673 on the control element. The medical device is close to the location on which it must be fixed. The fixing plug 51 comes into contact with the wall of the slot 661 in the inclined position. Because of the penetration movement of the medical device in the location, the fixing plug 51, sliding over the inclined surface of the slot 661, forces the retaining lock 66 to pivot about the axis 662 counter to the effect of the first spring 664. The first follower slides over the first bearing surface until it moves beyond it and loses contact. At this moment, the control element 67, under the effect of the second spring 674, passes from the unlocking position to the locking position. The end of the second guide finger, acting as the second follower, then comes into abutment against the second contact surface formed by the first guide finger 663. The control element then reaches the locking position. The retaining lock 66 for its part is in the retaining position and retains the fixing plug 51 in the slot 661, which is now perpendicular to the introduction movement, or even inclined beyond the perpendicular.

In the second alternative, the initial position is as follows:
  the security lock 692 is in the inactive position,
  the push button 69 is in the standby position,
  the transmission linkage 68 is in the retracted position, its first bearing surface in abutment against the retaining lock 66,
  the retaining lock 66 is in the retaining position.

The fixing plug 51 comes into contact with the inclined front edge of the retaining finger. Because of the penetration movement of the medical device in the location, the fixing plug 51, sliding over the inclined retaining finger, forces the retaining lock 66 to pivot about the axis 662 counter to the effect of the first spring 664. When the fixing plug moves beyond the retaining finger and loses contact, the retaining lock, under the effect of the first spring, passes from the free position to the retaining position and the retaining finger reaches the position in which it is behind the fixing plug 51.

The medical device is now situated in its location, locked in this position by the retaining lock 66, which retains the fixing plug 51. This is the situation shown in FIGS. 11b and 12a in which
  the security lock 692 is in the inactive position,
  the push button 69 is in the standby position,
  the transmission linkage 68 is in the retracted position,
  the control element 67, if available, is in the locking position, and
  the retaining lock 66 is in the retaining position.

In this position, the first bearing surface 681 is situated inside the recess 671, at a distance from the thrust edge. It may be situated against the edge of the recess opposite to this thrust edge.

When the medical worker wishes to remove the medical device and nothing is opposed to this, he merely has to press on the push button 69. The latter pushes the linkage 68 counter to the effect of the spring 683 from the retracted position to the advanced position. In the first alternative, the first end 681 of the linkage comes into contact with the first edge of the recess 671 of the control element. The linkage therefore forces the control element to pivot about the axis 672 and to pass from the locking position to the unlocking position counter to the effect of the second spring 674. In this pivot movement, the end of the second finger 673, acting as second follower, slides against the second guide surface formed by the first guide finger until it moves beyond it and loses contact. At this moment, the retaining lock 66, under the effect of the first spring 664, pivots from the retaining position into the free position. The fixing plug 51 is then released and it is possible to remove the medical device.

In the second alternative, the first end 681 of the linkage comes into contact with retaining lock 66. The linkage therefore forces the latter to pivot about the axis 662 and to pass from the retaining position to the free position counter to the effect of the first spring. The fixing plug 51 is then released and it is possible to remove the medical device.

Figure 12A:
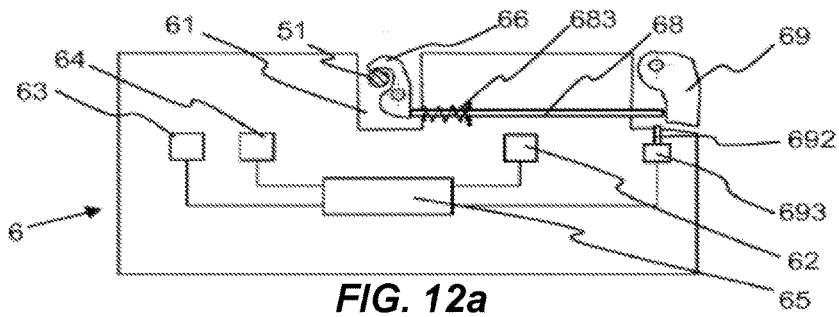
FIG. 12: a simplified schematic view of the functioning of the locking system according to the second embodiment.
Figure 12B:
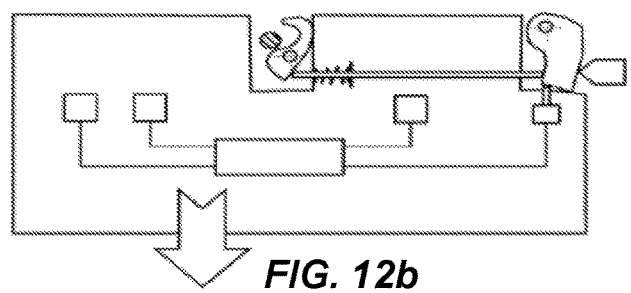
Figure 12C:
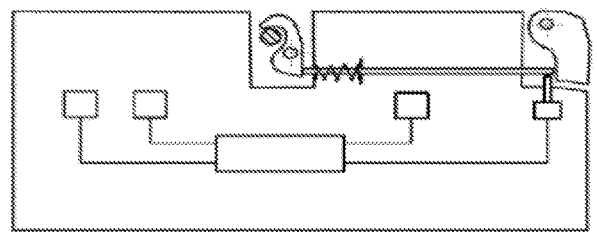
Figure 12D:
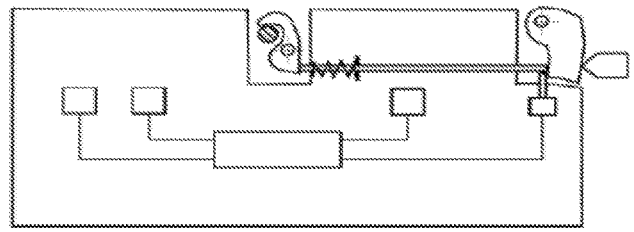
Figure 12E:
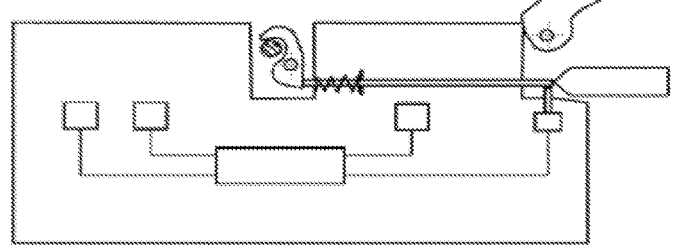

This is the situation shown in FIGS. 11a and 12b, in which:
  the security lock 592 is in the inactive position,
  the push button 69 is in the pressed-in position,
  the linkage 68 is in the advanced position,
  the control element 67, if available, is in the unlocking position, and
  the retaining lock 66 is in the free position.

The operator can then release the push button 69. The linkage is returned into the retracted position under the effect of the third spring 683, and therefore forces the push button 69 to pass in the standby position. Its first bearing surface 681, in the first alternative, leaves the thrust edge of the recess 671. However, the first finger of the retaining lock being in abutment against the first guide surface formed by the finger of the control element, the control element 67 cannot leave the unlocking position. Likewise, the retaining lock remains in the free position. In the second alternative, as soon as the transmission linkage returns into the retracted position under the effect of the third spring, the retaining lock 66 returns into the retaining position under the effect of the first spring.

This once again gives the initial position mentioned at the start of the process.

To prevent the operator from removing the medical device while it is in operation, the security lock 692 has been provided. Like the security lock 271 in the first embodiment, its movement is controlled by an actuator 692 that is connected to the electronic control unit 65. As long as the medical device can be removed, the security lock is situated in the inactive position and does not act on the movement of the push button. This is the situation shown in FIGS. 12a and 12b. When the control unit 65 starts the operation or has received the information that the medical device is operating, either alone or in combination with other devices, it sends a signal to the actuator 692 in order it moves the security lock to the active position. In this position, it is situated in the pivot path of the push button 69 and prevents it from moving in the direction of the pushed-in position. Consequently the operator cannot pivot the push button 69 or move the linkage 68. He cannot therefore release the fixing plug 51. This is the situation shown in FIGS. 12c and 12d. In order to enable the medical staff to be able to take over again, provision is made for the push button 69 to be able to be moved away from the standby position to a raised position that releases access to the second bearing surface 682. Since the latter is not situated in the field of action of the security lock, its movement is not interfered with by the latter. It is therefore possible for the personnel to press manually on the second bearing surface 682 in order to move the linkage as the push button would have done if had not been locked by the security lock 692 placed in the active position. This is the situation shown in FIG. 12e. By raising the push button, it is possible to get round the locking effect of the security lock 692 although it is still in the active position.

It goes without saying that it is possible to design the push button not in the form of a pivoting part but in the form of a part able to move in translation.

In both embodiments, a first detector can detect the attempts of the medical staff to unlock the first retaining lock 28, 66. If this is the case, the detector sends a signal to the electronic control unit. If the piston 271 is in the active position, and thus the second latch is in the retaining position (first embodiment), or if the rod 692 is in the active position (second embodiment), the electronic control unit sends a message to the control panel informing the user that the security lock 271, 692 is in the active position and that the pump is not to be removed. The message can also be a sound message. A second detector located e.g. at the second latch 26 or at the push button 69 can be provided for emitting an alarm message or an alarm sound when the security lock has been circumvented, e.g. when the second latch 26 is manually unlocked by circumventing the piston 271 or when the push button 69 is moved in the raised position and the linkage 68 manually moved despite the active position of the rod 692. Alternatively or in addition, the detector may also be part of the medical device and/or the holding structure.

The pull-knobs 264, 281 and the push button 69 can be replaced by any other mechanical device, e.g. a lever or a switch. The knobs 264, 281 can be designed so as the user has to push the unlocking device instead of pulling it. The push button 69 can be designed so as the user has to pull the unlocking device instead of pushing it. Likewise, they can be replaced by electric devices like drives actuated from the outside of the medical device by a switch or other means.

In the embodiments as illustrated in the figures, the piston 271 and the rod 692 constitute the security lock whereas the first retaining latch 28 and the hook 66 constitute the first retaining lock.

The actuators 27, 693 constitute the automatic control devices of the movement of the security lock (piston 271 and rod 692). In the first embodiment, the second pull-knob 264 associated to the spring 263 and the box 262 constitutes the second manual control mechanism for circumventing the effect of the security lock 271. The first pull-knob 281 constitutes the first manual control mechanism of the first retaining lock 28 (retaining latch). In the second embodiment, the push button 69, the linkage 68 and the control element 67 (if available) constitute as well the first manual control mechanism of the movement of the retaining lock 66 when the push button moves between the standby position and the pushed-in position, as the second manual control mechanism for circumventing the security lock when the push button is in the raised position.

Alternatively, the retaining lock and/or the security lock are not located at the medical device, but are part of the rack. For example, the locking system of the first embodiment may be located at the fixing plug 11. In the second embodiment, the fixing plug may be part of the medical device. The pull-knobs or the push button (or alternative means for acting on the latches) and the actuator are also part of the rack. Furthermore, a transmission system is being provided between the control unit of the medical device and the actuator in case that the control unit is part of the medical device, comprising for example a signal receiver on the actuator side and a signal transmitter on the medical device side. Alternatively, the control unit for controlling the security lock is part of the rack.

In another embodiment, the control of the security lock is handled by means of a central unit. Preferably, the central unit is a device apart from the medical device and the holding structure. Preferably, the central unit may be fixed to the holding structure. In one embodiment, the central unit controls the automatic control device directly, using its own control unit. Alternatively, the central unit controls the automatic control device via a control unit which is part of the holding structure or the medical device and which controls the automatic control device.

Instead of a mechanical manual control mechanism, the first retaining lock could, for example, like the security lock, also be moved by an actuator. The actuator could be controlled by the control unit of the medical device or by an additional control unit. A button, switch or other activating device could be provided at the medical device or holding structure to allow the medical staff to send a signal to the control unit in order to move the (first) retaining lock to the free position.

Although in the first embodiments described above the first and the second retaining locks comprise latches and recesses or in the second embodiment a hook and a fixing plug perpendicular to the approach movement of the medical device toward its location in the rack, the invention is not limited to such locks. Other kind of locks known by the person skilled in the art could be likewise used for carrying out the invention. Even non-mechanical locks, like magnetic locks, could be also used.

LIST OF REFERENCES

1 Rack
  11 Fixing plug (fixing element of the rack)
    111 Second recess
    112 Front face of the fixing plug
    113 First recess
    114 Annular groove
2 Medical device (pump)
  21 Socket (retaining structure of the medical device)
  22 Pumping mechanism
  23 Display
  24 Control panel
  25 Electronic control unit 26 First latch (first retaining lock)
  261 Rod
  262 Box
  263 Spring
  264 First pull-knob (manual control mechanism of the second retaining lock)
27 Actuator (automatic control device of the security lock)
  271 Piston (security lock)
28 Second latch (second retaining lock)
  281 Second pull-knob (manual control mechanism for the second retaining lock)
5 Rack
  51 Retaining plug (retaining element of the rack)
6 Medical device
  61 Socket (retaining structure of the medical device
  62 Pumping mechanism
  63 Display
  64 Control panel
  65 Electronic control unit
  66 Retaining lock
    661 Longitudinal slot
    662 Axis
    663 First guide finger ($1^{st}$ follower/$2^{nd}$ guide surface)
    664 First spring
  67 Control element
    671 Recess
    672 Axis
    673 Second guide finger ($2^{nd}$ follower/$1^{st}$ guide surface)
    674 Second spring
  68 Transmission linkage
    681 First bearing surface
    682 Second bearing surface
    683 Third spring
  69 Push button
    691 Axis
    692 Security lock (rod)
    693 Actuator

The invention claimed is:

1. A locking system for locking a medical device on a holding structure, the locking system comprises:
the medical device and the holding structure, each provided with retaining elements, which can cooperate with one another;
  a first retaining lock for retaining the medical device when connected to the holding structure, wherein the first retaining lock is movable by a first manual control mechanism between a retaining position, in which the first retaining lock retains the medical device on the holding structure to which the medical device is connected, and a free position, in which the first retaining lock does not retain the medical device on the holding structure to which it is connected; and
  a security lock which is movable by an automatic control device between an inactive position and an active position, wherein the security lock, in the active position, prevents the medical device from being removed from the holding structure to which the medical device is connected, and in the inactive position, the security lock does not prevent the medical device from being removed from the holding structure to which the medical device is connected;
wherein a second manual control mechanism is provided for circumventing the effect of the security lock so that the medical device is removeable from the holding structure to which the medical device is connected even if the security lock is in the active position.

2. The locking system according to claim 1, further comprising a detector for detecting the active position of the security lock.

3. The locking system according to claim 2, wherein a signal emitting device is provided for emitting a visual or audible signal when the detector detects that the security lock has been circumvented.

4. The locking system according to claim 1, wherein the automatic control device for moving the security lock comprises an actuator.

5. The locking system according to claim 1, wherein the locking system comprises a second retaining lock for retaining the medical device when connected to the holding structure, wherein the second retaining lock is movable by the security lock between a retaining position, in which the second retaining lock retains the medical device on the holding structure to which the medical device is connected, and a free position, in which the second retaining lock does not retain the medical device on said holding structure.

6. The locking system according to claim 5, wherein the second manual control mechanism for circumventing the effect of the security lock comprises
  a non-electric device which can be actuated from outside of the medical device and of the holding structure wherein the non-electric device is coupled to the second retaining lock; and
  a spring located between the second retaining lock and the security lock.

7. The locking system according to claim 6, wherein the non-electric device comprises a pull-knob.

8. The locking system according to claim 5, wherein the second manual control mechanism for circumventing the effect of a security latch comprises an electrical device which can be actuated from outside of the medical device and of the holding structure.

9. The locking system according to claim 5, wherein the first manual control mechanism for moving the first retaining lock comprises a non-electric device, which is accessible from the outside of the medical device and of the holding structure wherein the non-electric device is coupled to the first retaining lock.

10. The locking system according to claim 5, wherein the first manual control mechanism for moving the first retaining lock comprises an electric device, which can be actuated from outside of the medical device and of the holding structure.

11. The locking system according to claim 5, wherein the first retaining lock is held by a spring in the retaining position in absence of any external influence.

12. The locking system according to claim 5, wherein the first retaining lock and the second retaining lock each comprises a latch which is located at the retaining element of the medical device or of the holding structure, wherein each latch is shaped and located in such a way to be able to engage a corresponding recess, which is provided at the retaining element of the holding structure or of the medical device, when the medical device is connected to such a holding structure.

13. The locking system according to claim 1, wherein the security lock, in the active position, prevents the first manual control mechanism for moving the retaining lock in the free position.

14. The locking system according to claim 13, wherein the first manual control mechanism comprises a push button, a transmission linkage and a control element, wherein the push button can move between a standby position and a pushed-in position, wherein the transmission linkage can move between a retracted position and an advanced position, wherein a spring tends to return the transmission linkage into the retracted position, wherein the transmission linkage, in the retracted position, pushes the push button into the standby position, wherein the push button, in the pushed-in position, pushes the transmission linkage into the advanced position against the effect of the spring operating on said transmission linkage, wherein the control element can move from a locking position, in which the control element locks the retaining lock in the retaining position, and a unlocking position, in which the control element does not lock the retaining lock in the retaining position, wherein a spring tends to return the control element in the locking position, and wherein the transmission linkage, when moving from the retracted position to the advanced position, moves the control element in the unlocking position.

15. The locking system according to claim 14, wherein the security lock, in the active position, is situated in the passage used by the push button to pass from the standby position to the pushed-in position such that the push button comes into abutment against the security lock before reaching the pushed-in position.

16. The locking system according to claim 14, wherein the push button is designed to be able to move beyond the standby position into a raised position opposite to the pushed-in position, wherein in the raised position of the push button, the transmission linkage may be actuated from outside of the medical device and of the holding structure although the security lock is in the active position.

17. The locking system according to claim 13, wherein the first manual control mechanism comprises a push button and a transmission linkage, wherein the push button can move between a standby position and a pushed-in position, wherein the transmission linkage can move between a retracted position and an advanced position, wherein a spring tends to return the transmission linkage into the retracted position, wherein the transmission linkage, in the retracted position, pushes the push button into the standby position, wherein the push button, in the pushed-in position, pushes the transmission linkage into the advanced position against the effect of the spring operating on said transmission linkage, and wherein the transmission linkage, when moving from the retracted position to the advanced position, moves the retaining lock in the free position.

18. The locking system according to claim 1, wherein the first retaining lock, a second retaining lock, and the security lock are located at the fixation element of the medical device.

19. The locking system according to claim 1, wherein the first retaining lock, a second retaining lock, and the security lock are located at the fixation element of the holding structure.

20. A medical device comprising a retaining element for connecting the medical device with a corresponding retaining element of a holding structure, wherein the medical device is provided with the locking system according to claim 1.

21. A holding structure for holding a medical device, wherein the holding structure comprises a retaining element to which a corresponding retaining element of the medical device can be connected, wherein the holding structure is provided with a locking system according to claim 1.

22. A method for controlled locking of a medical device with a holding structure by means of a locking system according to claim 1, wherein
 the security lock is moved by the automatic control device from the inactive position to the active position at the beginning of a procedure during which the medical device is not removeable from the holding structure, and
 the security lock is moved by the automatic control device from the active position to the inactive position when the medical device can be removed from the holding structure;
 the automatic control device being controlled by the electronic control unit.

23. The method according to claim 22, wherein effect of the security lock is circumvented by a second manual control mechanism.

24. The method according to claim 23, the effect of the security lock is circumvented by moving the second retaining lock in the free position.

25. The method according to claim 23, wherein the security lock is circumvented by moving a push button from a standby position to a raised position in such a way that a transmission linkage may be actuated from the outside of the medical device and the holding structure.

26. The locking system according to claim 1, further comprising a detector for detecting the active position of the security lock.

27. The locking system according to claim 1, wherein the locking system comprises a second retaining lock for retaining the medical device when connected to the holding structure, wherein the second retaining lock is movable by the security lock between a retaining position, in which the second retaining lock retains the medical device on the holding structure to which the medical device is connected, and a free position, in which the second retaining lock does not retain the medical device on said holding structure.

* * * * *